(12) United States Patent
Stirton

(10) Patent No.: US 6,614,540 B1
(45) Date of Patent: Sep. 2, 2003

(54) METHOD AND APPARATUS FOR DETERMINING FEATURE CHARACTERISTICS USING SCATTEROMETRY

(75) Inventor: James Broc Stirton, Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 33 days.

(21) Appl. No.: 09/894,048

(22) Filed: Jun. 28, 2001

(51) Int. Cl.$^7$ .......................... G01B 11/28; G01N 21/00
(52) U.S. Cl. ..................................... 356/630; 356/237.1
(58) Field of Search ............................... 356/630, 237.1

(56) References Cited

U.S. PATENT DOCUMENTS

| | | | |
|---|---|---|---|
| 3,829,220 A | * | 8/1974 | Parkinson .................. 356/640 |
| 6,051,348 A | | 4/2000 | Marinaro et al. ............. 430/30 |
| 6,245,584 B1 | | 6/2001 | Marinaro et al. ............. 438/14 |
| 6,433,871 B1 | * | 8/2002 | Lensing et al. ............. 356/381 |
| 6,433,878 B1 | | 8/2002 | Niu et al. .................... 356/603 |
| 2002/0135781 A1 | | 9/2002 | Singh et al. ................. 356/601 |

* cited by examiner

*Primary Examiner*—Scott J. Sugarman
(74) *Attorney, Agent, or Firm*—Williams, Morgan & Amerson, P.C.

(57) ABSTRACT

A method for characterizing features includes measuring a dimensional characteristic of a first grating structure; illuminating at least a portion of a first feature and the first grating structure, the first feature being formed over at least a portion of the first grating structure; measuring light reflected from the illuminated portion of the first feature and the first grating structure to generate a reflection profile; selecting at least one reference reflection profile based on the measured dimensional characteristic of the first grating structure, comparing the generated reflection profile to the selected reference reflection profile; and determining a characteristic of the first feature based on the comparison between the measured reflection profile and the selected reference reflection profile.

70 Claims, 8 Drawing Sheets

METHOD AND APPARATUS FOR DETERMINING FEATURE CHARACTERISTICS USING SCATTEROMETRY

BACKGROUND OF THE INVENTION

1. Field of the Invention

This invention relates generally to the field of semiconductor device manufacturing and, more particularly, to a method and apparatus for determining feature characteristics using scatterometry.

2. Description of the Related Art

There is a constant drive within the semiconductor industry to increase the quality, reliability and throughput of integrated circuit devices, e.g., microprocessors, memory devices, and the like. This drive is fueled by consumer demands for higher quality computers and electronic devices that operate more reliably. These demands have resulted in a continual improvement in the manufacture of semiconductor devices, e.g., transistors, as well as in the manufacture of integrated circuit devices incorporating such transistors. Additionally, reducing the defects in the manufacture of the components of a typical transistor also lowers the overall cost per transistor as well as the cost of integrated circuit devices incorporating such transistors.

The technologies underlying semiconductor processing tools have attracted increased attention over the last several years, resulting in substantial refinements. However, despite the advances made in this area, many of the processing tools that are currently commercially available suffer certain deficiencies. In particular, such tools often lack advanced process data monitoring capabilities, such as the ability to provide historical parametric data in a user-friendly format, as well as event logging, real-time graphical display of both current processing parameters and the processing parameters of the entire run, and remote, i.e., local site and worldwide, monitoring. These deficiencies can engender nonoptimal control of critical processing parameters, such as throughput, accuracy, stability and repeatability, processing temperatures, mechanical tool parameters, and the like. This variability manifests itself as within-run disparities, run-to-run disparities and tool-to-tool disparities that can propagate into deviations in product quality and performance, whereas an ideal monitoring and diagnostics system for such tools would provide a means of monitoring this variability, as well as providing means for optimizing control of critical parameters. Semiconductor devices are manufactured from wafers of a substrate material. Layers of materials are added, removed, and/or treated during fabrication to create the electrical circuits that make up the device. The fabrication essentially comprises four basic operations. Although there are only four basic operations, they can be combined in hundreds of different ways, depending upon the particular fabrication process.

The four operations typically used in the manufacture of semiconductor devices are:

- layering, or adding thin layers of various materials to a wafer from which a semiconductor device is produced;
- patterning, or removing selected portions of added layers;
- doping, or placing specific amounts of dopants in the wafer surface through openings in the added layers; and
- heat treatment, or heating and cooling the materials to produce desired effects in the processed wafer.

Among the important aspects in semiconductor device manufacturing are rapid thermal annealing (RTA) control, chemical-mechanical polishing (CMP) control, etch control, and photolithography control. As technology advances facilitate smaller critical dimensions for semiconductor devices, the need for reduction of errors increases dramatically. Proper formation of sub-sections within a semiconductor device is an important factor in ensuring proper performance of the manufactured semiconductor device. Critical dimensions of the sub-sections generally have to be within a predetermined acceptable margin of error for semiconductor devices to be within acceptable manufacturing quality.

An important aspect of semiconductor manufacturing is overlay control. Overlay is one of several important steps in the photolithography area of semiconductor manufacturing. Overlay control involves measuring the misalignment between two successive patterned layers on the surface of a semiconductor device. Generally, minimization of misalignment errors is important to ensure that the multiple layers of the semiconductor devices are connected and functional. As technology facilitates smaller critical dimensions for semiconductor devices, the need for the reduction of misalignment errors increases dramatically.

Generally, a set of photolithography steps is performed on a lot of wafers using a semiconductor manufacturing tool commonly referred to as an exposure tool or a stepper. The manufacturing tool communicates with a manufacturing framework or a network of processing modules. The manufacturing tool is generally connected to an equipment interface. The equipment interface is connected to a machine interface to which the stepper is connected, thereby facilitating communications between the stepper and the manufacturing framework. The machine interface may generally be part of an advanced process control (APC) system. The APC system initiates a control script, which can be a software program that automatically retrieves the data needed to execute a manufacturing process. The input parameters that control the manufacturing process are revised periodically in a manual fashion. As the need for higher precision manufacturing processes are required, improved methods are needed to revise input parameters that control manufacturing processes in a more automated and timely manner.

The present invention is directed to overcoming, or at least reducing the effects of, one or more of the problems set forth above.

SUMMARY OF THE INVENTION

One aspect of the present invention is seen in a method for characterizing features. The method includes measuring a dimensional characteristic of a first grating structure illuminating at least a portion of a first feature and the first grating structure, the first feature being formed over at least a portion of the first grating structure; measuring light reflected from the illuminated portion of the first feature and the first grating structure to generate a reflection profile selecting at least one reference reflection profile based on the measured dimensional characteristic of the first grating structure; comparing the generated reflection profile to the selected reference reflection profile; and determining a characteristic of the first feature based on the comparison between the measured reflection profile and the selected reference reflection profile.

Another aspect of the present invention is seen in a processing line including a first metrology tool and a second metrology tool. The first metrology tool is adapted to measure a dimensional characteristic of a first grating structure. The second metrology tool includes a light source, a detector, and a data processing unit. The light source is adapted to illuminate at least a portion of a first feature and the first grating structure. The first feature is formed over at least a portion of the first grating structure. The detector is adapted to measure light reflected from the illuminated portion of the first feature and the first grating structure to generate a reflection profile, The data processing unit is adapted to select at least one reference reflection profile based on the measured dimensional characteristic of the first grating structure, comparing the generated reflection profile to the selected reference reflection profile, and determine a characteristic of the first feature based on the comparison between the measured reflection profile and the selected reference reflection profile.

BRIEF DESCRIPTION OF THE DRAWINGS

The invention may be understood by reference to the following description taken in conjunction with the accompanying drawings, in which like reference numerals identify like elements, and in which.

Figure 1:
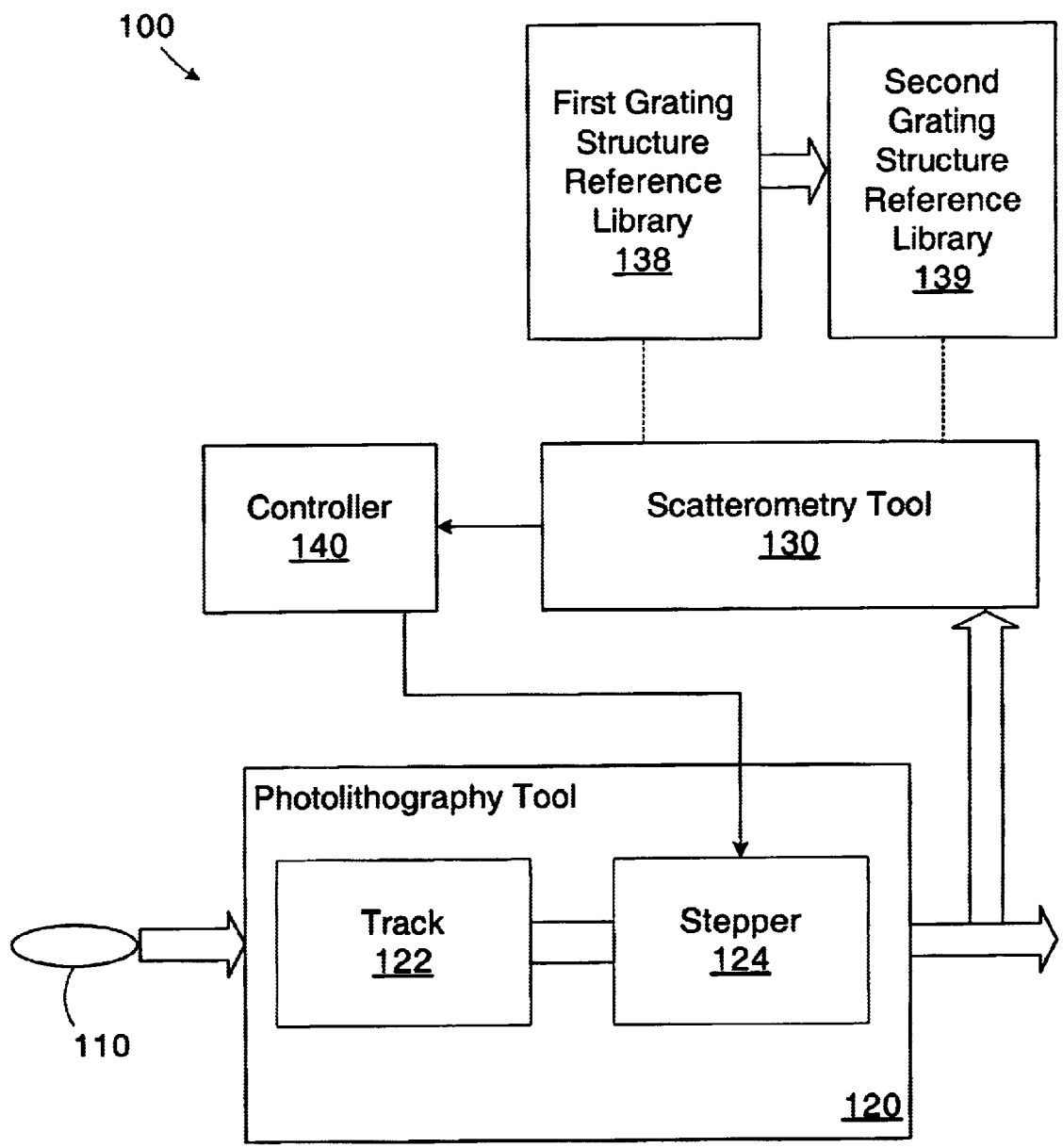
FIG. 1 is a simplified diagram of an illustrative processing line for processing wafers in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Overlay control is an important step in semiconductor manufacturing. In particular, overlay control involves measuring misalignment errors between semiconductor layers during manufacturing processes. Improvements in overlay control could result in substantial enhancements, in terms of quality and efficiency, in semiconductor manufacturing processes. The present invention provides a method of implementing automated error correction for control of overlay error. Furthermore, the present invention provides a method of controlling overlay registration on a run-to-run basis.

Referring to FIG. 1, a simplified diagram of an illustrative processing line 100 for processing wafers 110 in accordance with one illustrative embodiment of the present invention is provided. The processing line 100 includes a photolithography tool 120 for forming a pattern in a photoresist layer formed on the wafer 110. The photolithography tool 120 includes a track 122 coupled to a stepper 124. The track 122 spins photoresist material onto the wafer 110 and pre-bakes the photoresist layer. The stepper 124 exposes the photoresist layer to form a pattern in the photoresist layer. The track 122 then performs a post-exposure bake (i.e., if necessary for the type of photoresist layer used) and applies a developer solution to remove the exposed portions of the photoresist layer (i.e., for a positive-type photoresist material) to generate a pattern in the photoresist layer. The photoresist layer is typically used as a mask for a subsequent etch process used to form features on the wafer 110 or as a mask for performing an implantation process (e.g., for doping a substrate to form active regions).

The processing line 100 also includes a scatterometry tool 130 adapted to determine overlay errors in photoresist patterns formed by the photolithography tool 120. In general, the scatterometry tool 130 includes optical hardware, such as an ellipsometer or reflectometer, and a data processing unit loaded with a scatterometry software application for processing data collected by the optical hardware. For example, the optical hardware may include a model OP5140 or OP5240 with a spectroscopic ellipsometer offered by Therma-Wave, Inc. of Freemont, Calif. The data processing unit may comprise a profile application server manufactured by Timbre Technologies, a subsidiary of Tokyo Electron Limited, Inc. of Tokyo, Japan and distributed by Therma-Wave, Inc. The scatterometry tool 130 may be external or, alternatively, the scatterometry tool 130 may be installed in an in-situ arrangement.

A controller 140 is provided for providing feedback to the photolithography tool 120 based on the measurements generated by the scatterometry tool 130. The controller 140 adjusts the operating recipe of the stepper 124 to correct for overlay errors. In the illustrated embodiment, the controller 140 is a computer programmed with software to implement the functions described. However, as will be appreciated by those of ordinary skill in the art, a hardware controller designed to implement the particular functions may also be used. Moreover, the functions performed by the controller 140, as described herein, may be performed by multiple controller devices distributed throughout a system. Additionally, the controller 140 may be a stand-alone controller, it may be integrated into a tool, such as the photolithography tool 120, or the scatterometry tool 130, or it may be part of a system controlling operations in an integrated circuit manufacturing facility.

Portions of the invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

An exemplary software system capable of being adapted to perform the functions of the controller 140, as described, is the Catalyst system offered by KLA-Tencor, Inc. The Catalyst system uses Semiconductor Equipment and Materials International (SEMI) Computer Integrated Manufacturing (CIM) Framework compliant system technologies and is based on the Advanced Process Control (APC) Framework. CIM (SEMI E81-0699—Provisional Specification for CIM Framework Domain Architecture) and APC (SEMI E93-0999—Provisional Specification for CIM Framework Advanced Process Control Component) specifications are publicly available from SEMI.

Wafers 110 are processed in the stepper 124 using a plurality of control input signals. In the illustrated embodiment, the control inputs signals used to configure the stepper 124 include an x-translation signal, a y-translation signal, an x-expansion wafer scale signal, a y-expansion wafer scale signal, a reticle magnification signal, and a reticle rotation signal. Generally, errors associated with the reticle magnification signal and the reticle rotation signal relate to a particular exposure process on the surface of the wafer being processed in the exposure tool. The controller 140 is adapted to update the control input signals based on overlay error measurements performed by the scatterometry tool 130 on a run-to-run basis.

When the stepper 124 completes processing of a wafer 110, the wafer 110 is examined by the scatterometry tool 140. The wafer may be examined prior to developing of the photoresist layer (i.e., using the latent photoresist image) or after the developing process (i.e., using the photoresist pattern). The scatterometry tool 140 provides a measurement of misregistration that was present in the previous exposure step. The amount of misregistration relates to the misalignment in the photolithography process that occurred between two layers formed on the wafer.

Figure 2A:
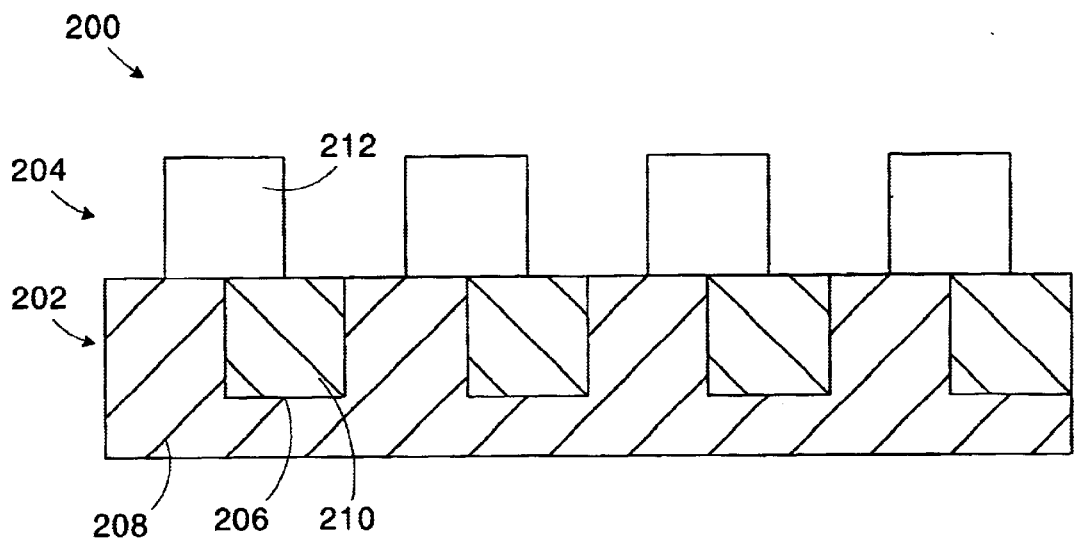
FIGS. 2A, 2B, and 2C are cross section views of exemplary structures that may be used to measure overlay errors in the processing line of FIG. 1.
Figure 2B:
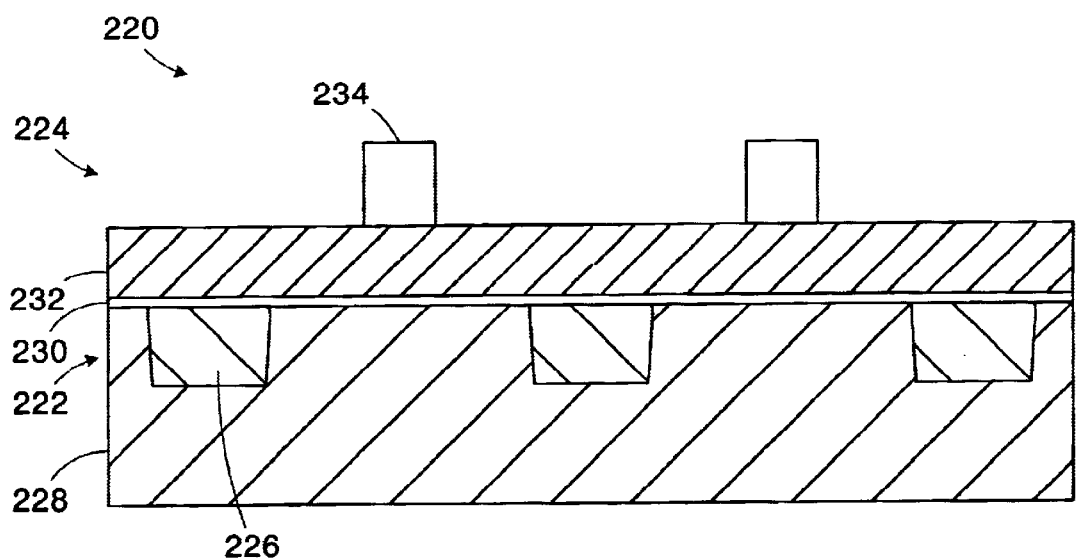
Figure 2C:
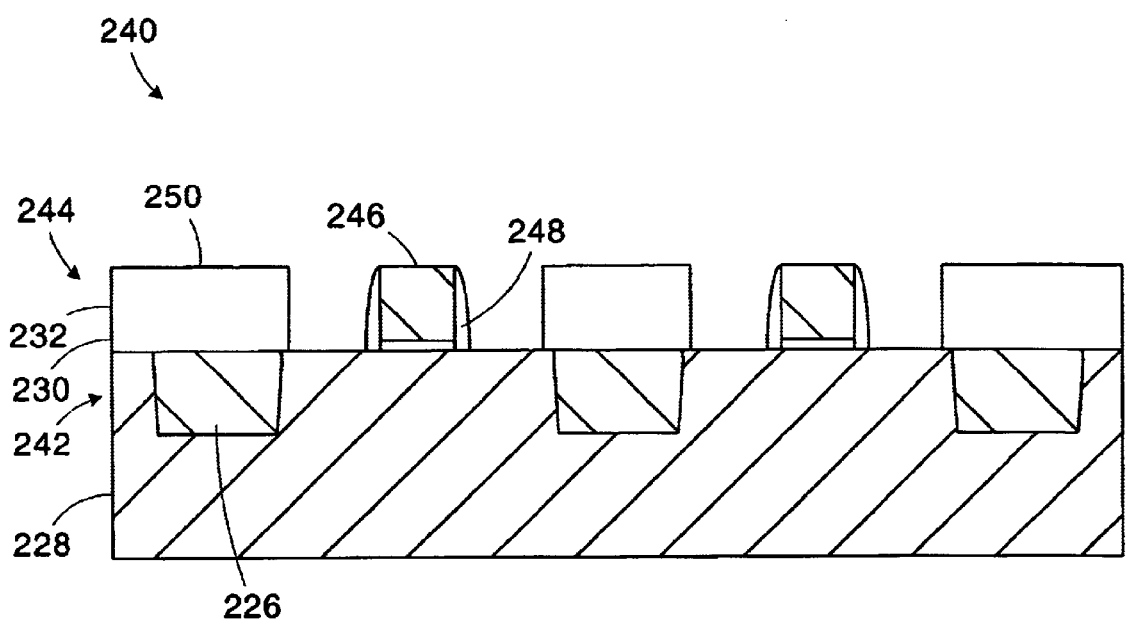

Turning now to FIGS. 2A–2C, cross section views of exemplary structures 200, 220, 240 that may be used to measure overlay errors in the processing line of FIG. 1 are shown. The structures 200, 220, 240 of FIGS. 2A–2C may be features formed in production devices, or alternatively, a test structure having the same general configuration as production features formed on the wafer 110 may be employed. The test structures, if employed, may be formed in a region of the wafer 110 not normally used for forming devices (e.g., in the periphery region where identification codes are typically scribed or in the scribe lines between production die). The wafer 110 may include multiple structures 200, 220, 240 having differing orientations for measuring the overlay error in different directions (e.g., X and Y).

FIG. 2A is a cross section view of the structure 200 including a first grating structure 202 and a second grating structure 204. The first grating structure 202 may be formed by etching trenches 206 in a base layer 208, such as a substrate layer, and filling the trenches 206 with a fill material 210, such as silicon dioxide. Of course, other techniques may be employed for forming the first grating structure 202. For example, an implantation process may be used to form an alternating pattern of doped and undoped material to form the grating structure. In the illustrated embodiment, the second grating structure 204 is a patterned and developed photoresist layer 212. In an alternative embodiment, the second grating structure 204 may be an exposed photoresist layer (not shown) prior to development. The second grating structure 204 may be defined by the latent photoresist pattern (i.e., the exposed and non-exposed portion have different optical characteristics and thus refract light differently). Using the structure 200, the scatterometry tool 130 is adapted to measure the misregistration between the first and second grating structures 202, 204 to provide an overlay error, and the controller 140 is adapted to control the photolithography tool 220 for subsequently patterned photoresist layers 212 to correct the overlay error.

FIG. 2B is a cross section view of the structure 220 including a first grating structure 222 and a second grating structure 224. The first grating structure 222 includes shallow trench isolation (STI) structures 226 (i.e., trenches filled with silicon dioxide) in a substrate layer 228. A gate oxide layer 230 is formed over the substrate layer 228, and a polysilicon layer 232 is formed over the gate oxide layer 230. The second grating structure 224 is formed from a patterned and developed photoresist layer 234. Again, the second grating structure 224 may be an exposed photoresist layer (not shown) prior to development. The photoresist layer 234 is subsequently used as a mask to etch gate electrode stacks from the gate oxide layer 230 and the polysilicon layer 232. Using the structure 220, the scatterometry tool 130 is adapted to measure the misregistration between the first and second grating structures 222, 224 to provide an overlay error (i.e., gate to STI overlay error), and the controller 140 is adapted to control the photolithography tool 220 for subsequently patterned photoresist layers 234 to correct the overlay error.

FIG. 2C is a cross section view of the structure 240 including a first grating structure 242 and a second grating structure 244. The first grating structure 242 represents the structure of FIG. 2B after etching of gate electrode stacks 246 and after sidewall spacers 248 have been formed adjacent the gate electrode stack 246. The second grating structure 244 is formed from a patterned and developed photoresist layer 250. Again, the second grating structure 244 may be an exposed photoresist layer (not shown) prior to development. The photoresist layer 250 is subsequently used as a mask for an implantation process to form source drain regions proximate the etch gate electrode stacks 246. Using the structure 240, the scatterometry tool 130 is adapted to measure the misregistration between the first and second grating structures 242, 244 to provide an overlay error (i.e., implant mask to gate overlay error), and the controller 140 is adapted to control the photolithography tool 220 for subsequently patterned photoresist layers 250 to correct the overlay error.

Figure 3A:
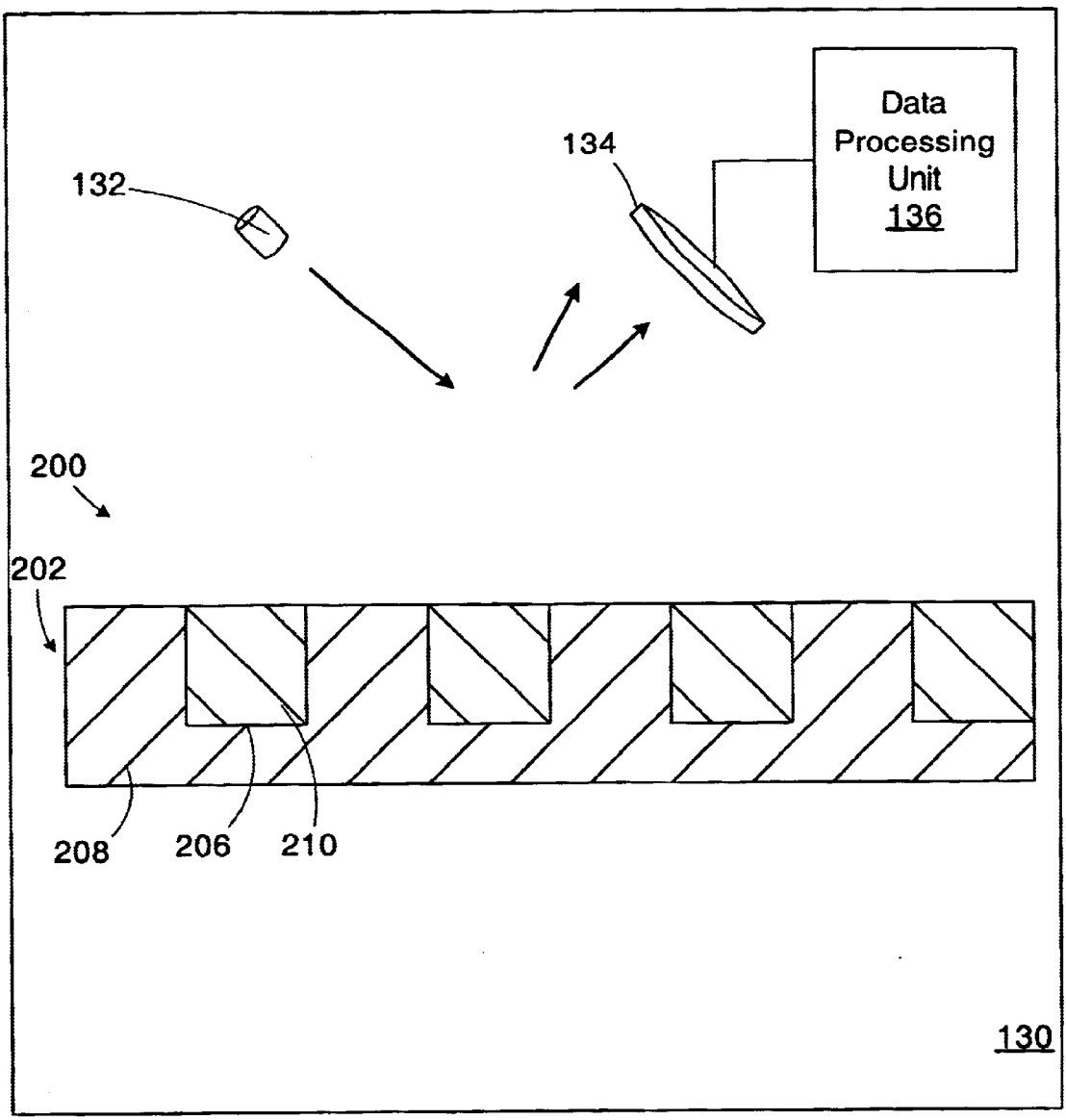
FIGS. 3A and 3B are a simplified views of the scatterometry tool of FIG. 1.
Figure 3B:
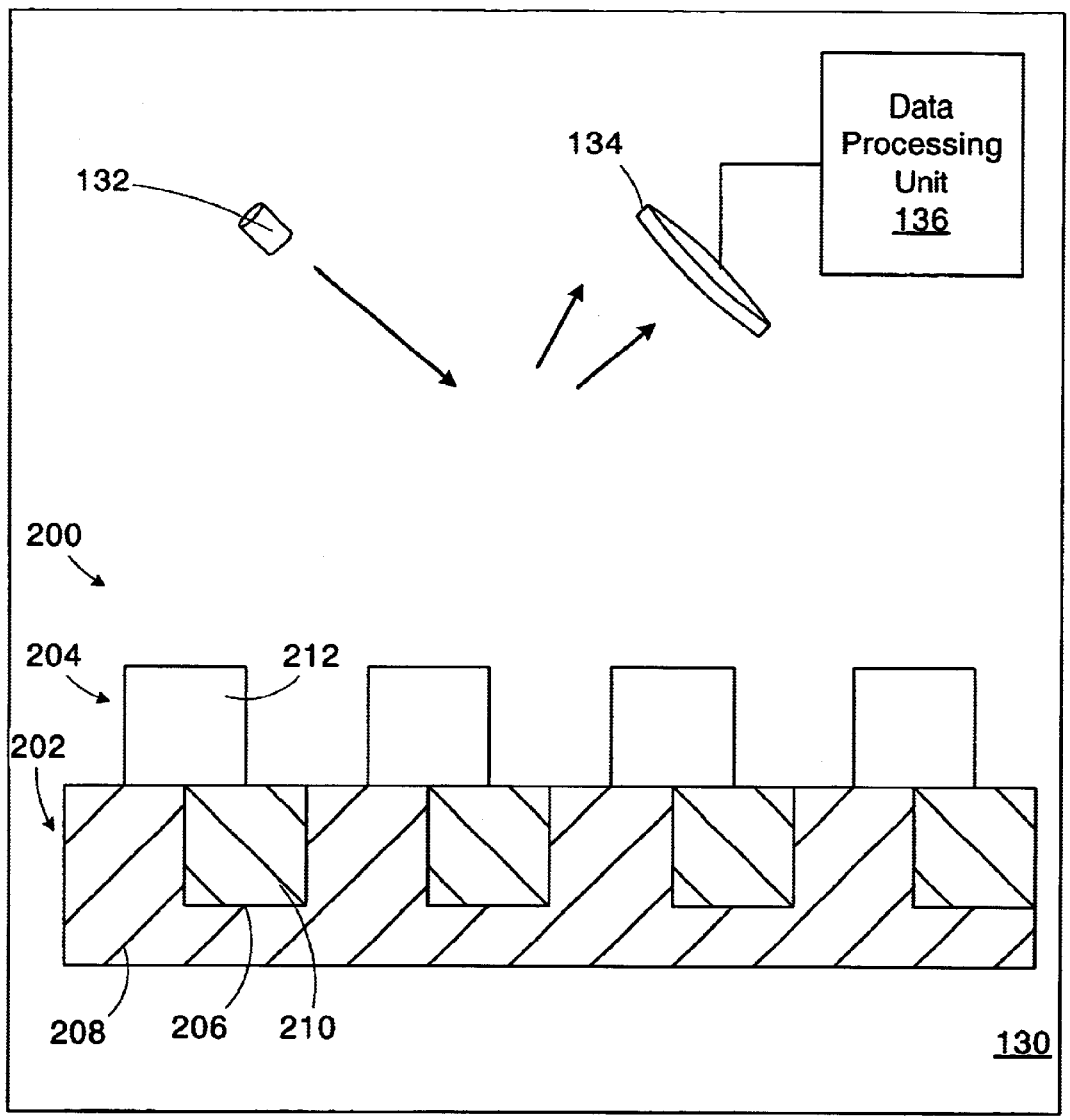

Turning now to FIGS. 3A and 3B, the operation of the scatterometry tool 130 is described as it may be used to measure overlay error using the structure 200 of FIG. 2A. Of course, the scatterometry tool 130 may be employed in a similar manner to determine overlay errors in the structures 220, 240, of FIGS. 2B and 2C, or in other structures having multiple overlaying grating structures. In one illustrated embodiment, the scatterometry tool 130 is adapted to measure the characteristics of the first grating structure 202 prior to formation of the second grating structure 204. Characterizing the first grating structure 202 allows a more accurate determination of the characteristics of the second grating structure 204.

The scatterometry tool 130, includes a light source 132 and a detector 134 positioned proximate the first grating structure 202 of the structure 200. The light source 132 of the scatterometry tool 130 illuminates at least a portion of the first grating structure 202, and the detector 134 takes optical measurements, such as intensity or phase, of the reflected light. A data processing unit 136 receives the optical measurements from the detector 134 and processes the data to identify dimensions of the first grating structure 202.

The scatterometry tool 130 may use monochromatic light, white light, or some other wavelength or combinations of wavelengths, depending on the specific implementation. The angle of incidence of the light may also vary, depending on the specific implementation. The light analyzed by the scatterometry tool 130 typically includes a reflected component (i.e., incident angle equals reflected angle) and a refracted component (i.e., incident angle does not equal the reflected angle). For purposes of discussion here, the term "reflected" light is meant to encompass both components. Dimensional variations cause changes in the reflection profile (e.g., intensity vs. wavelength–$\tan(\delta)$, phase vs. wavelength–$\cos(\psi)$, where $\delta$ and $\psi$ are common scatterometry outputs known to those of ordinary skill in the art) measured by the scatterometry tool 130.

Figure 4A:
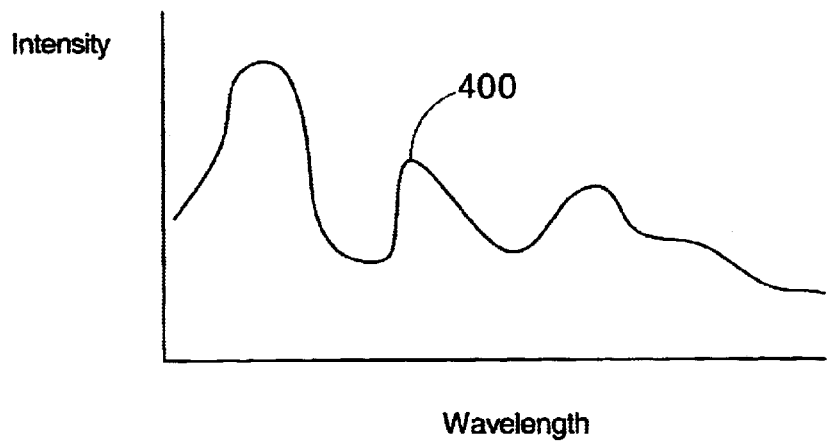
FIGS. 4A, 4B, and 4C illustrate a library of exemplary scatterometry curves used to characterize the wafer measured in the scatterometry tool of FIG. 3.
Figure 4B:
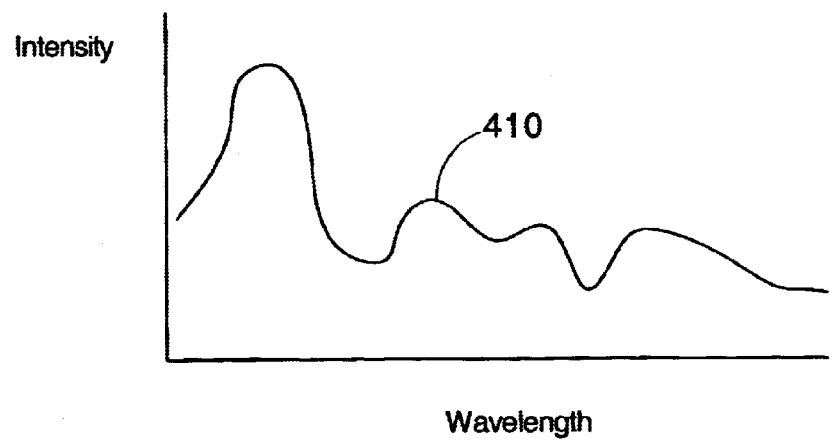
Figure 4C:
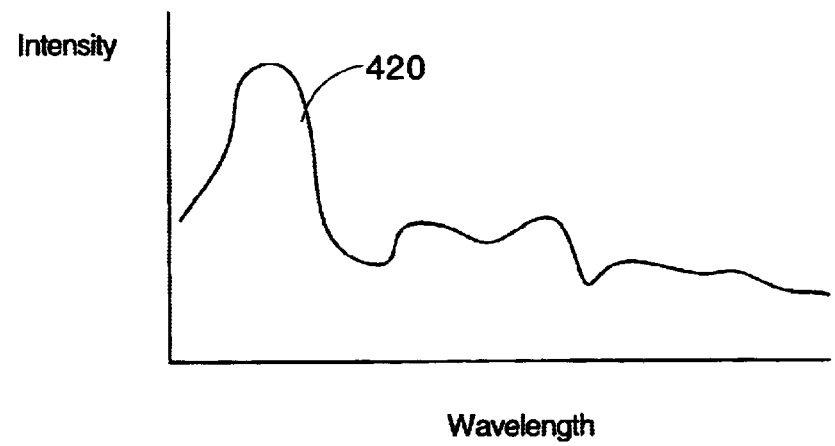

FIGS. 4A, 4B, and 4C illustrate exemplary reflection profiles 400, 410, 420 that may be included in a first grating structure reference library 138 (see FIG. 1) used by the data processing unit 136 to characterize the first grating structure 202 based on the reflection profiles measured by the scatterometry tool 130. The particular reflection profile expected for any structure depends on the specific geometry of the first grating structure 202 and the parameters of the measurement technique employed by the scatterometry tool 130 (e.g., light bandwidth, angle of incidence, etc.). The profiles in the first grating structure reference library 138 are typically calculated theoretically by employing Maxwell's equations to model individual spectra based on the expected characteristics of the first grating structure 202. Spectra are generated at a pre-determined resolution for many, if not all, profiles that may be expected, and the sum of all said spectra constitute the first grating structure reference library 138. Scatterometry libraries are commercially available from Timbre Technologies, Inc. The profiles in the first grating structure reference library 138 may also be generated empirically by measuring reflection profiles of sample wafers and subsequently characterizing the measured wafers by destructive or non-destructive examination techniques.

The reflection profiles 400, 410, 420 of FIGS. 4A, 4B, and 4C represent exemplary reflection profiles for the first grating structure reference library 138 with varying dimensional characteristics (e.g., trench width, trench depth, line width, sidewall angle, etc.). The reflection profiles of structures different amounts of variation may be included in the first grating structure reference library 138.

The data processing unit 136 receives a reflection profile measured by the detector 134 and compares it to the first grating structure reference library 138. Each reference profile has an associated grating structure metric related to the dimensions of the first grating structure 202. For example, the grating structure metric may comprise actual diameter, line widths, height, and/or sidewall angle measurements. The data processing unit 136 determines the reference reflection profile having the closest match to the measured reflection profile. Techniques for matching the measured reflection profile to the closest reference reflection profile are well known to those of ordinary skill in the art, so they are not described in greater detail herein. For example, a least squares error technique may be employed.

After determining the dimensions of the first grating structure 202, the scatterometry tool 130 is employed to measure the characteristics of the second grating structure 204, as shown in FIG. 3B. The scatterometry tool 130 uses a second grating structure reference library 139 in a similar fashion as described above in reference to FIGS. 3A, 4A, 4*b*, and 4C. However, the data processing unit 136 uses the data collected about the first grating structure 202 in evaluating the determining the dimensional characteristics of the second grating structure 204. Each entry in the second grating structure reference library 139 has an associated overlay metric. The data processing unit 136 identifies the closest entry in the second grating structure reference library 139 and uses the overlay metric to generate an overlay error measurement.

In one embodiment, the data processing unit 136 generates the second grating structure reference library 139 based on the dimensional characteristics of the first grating structure 202. The data-processing unit 136 holds the dimensions of the first grating structure 202 constant and generates entries in the second grating structure reference library 139 for differing degrees of overlay error in the second grating structure 204 assuming the known configuration of the first grating structure 202 (i.e., using Maxwell's equations). The data processing unit 136 then matches the measured reflection profile to the generated reflection profiles in the second grating structure reference library 139 to determine the overlay error.

In another embodiment, the second grating structure reference library 139 is divided into sub-libraries or sets. Each sub-library is associated with a particular first grating structure 202 configuration. For example, a sub-library may be created for a first grating structure 202 having a particular range of dimensions (e.g., trench depth or line width of between X and Y microns). The data processing unit 136 determines the sub-library associated with the measured characteristics of the first grating structure 202 and matches the measured reflection profile with the profiles in the sub-library to determine the overlay error.

In still another embodiment, the characterization of the first grating structure 202 may be conducted using other metrology tools, such as scanning electron microscopes, atomic force microscopes, or thickness measuring tools (e.g., Optiprobe tool offered by Therma-Wave). The data processing unit 136 uses the collected metrology data to generate the second grating structure reference library 139 or select the appropriate sub-library from the second grating structure reference library 139 as described above.

In yet another embodiment, the measured reflection profile may be compared to a target reflection profile selected from the second grating structure reference library 139 for a second grating structure 204 having known and desired dimensions. For example, the data processing unit 136 may generate a target reflection profile for the structure 200 including a second grating structure 204 having no, or at least acceptable amounts of overlay using Maxwell's equations and fixing the previously measured characteristics of the first grating structure 202. Alternatively, a target reflection profile may be calculated in advance for each range of dimensions for the first grating structure 202 (i.e., similar to the sub-library technique described above).

The measured reflection profile generated by the scatterometry tool 130 may then be compared to the target reflection profile. Based upon this comparison, a relatively rough approximation of the overlay error may be determined. That is, by comparing the measured reflection profile to the target reflection profile, the overlay error may be approximated, such that further matching of the measured reflection profile with additional reference reflection profiles is unwarranted. Using this technique, an initial determination may be made as to the overlay error. Of course, this step may be performed in addition to the matching or correlating of a measured reflection profile to a reference reflection profile from the second grating structure reference library 139 as described above. Similarly, the characterization of the first grating structure 202 may also be conducted by comparing the measured reflection profile of the first grating structure (see FIG. 3A) with a target reflection profile to approximate the dimensions of the first grating structure 202.

Although, the two-stage technique is described as it may implemented for measuring overlay error, the techniques may be employed for measuring other features where the characteristics of an underlying layer affect the ability of the scatterometry tool 130 to characterize an upper layer. For example, the conformality or thickness of a process layer formed over a grating structure may be measured by the scatterometry tool 130 (e.g., a spacer oxide layer formed over a gate electrode stack). The dimensions of the underlying grating structure may affect the measurements of the upper layer.

Figure 5:
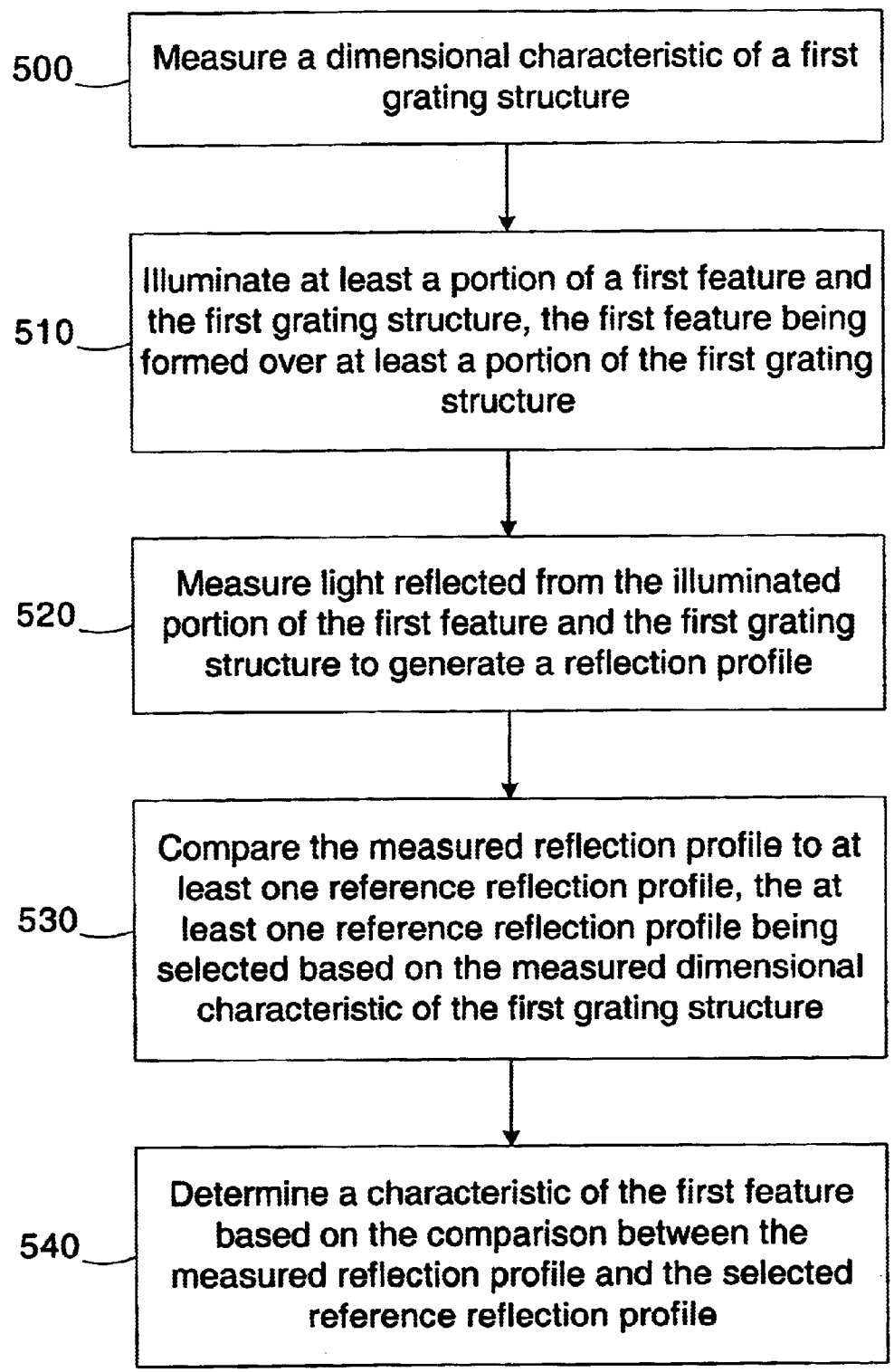
FIG. 5 is a simplified flow diagram of a method for determining characteristics of a feature in accordance with another illustrative embodiment of the present invention.
Figure 6:
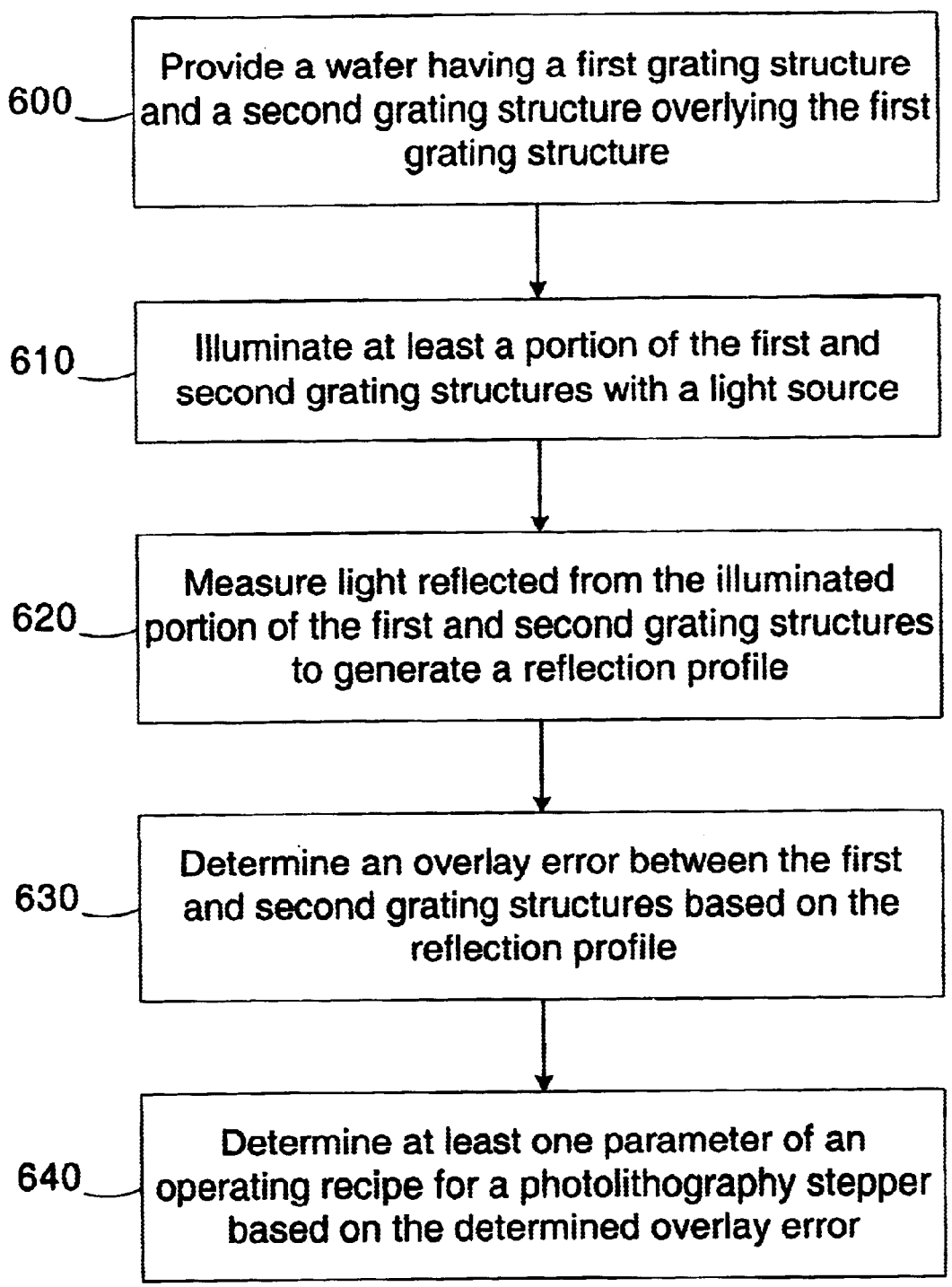
FIG. 6 is a simplified flow diagram of a method for controlling a photolithography process in accordance with another illustrative embodiment of the present invention.

The general, two-stage technique is described in reference to FIG. 5, which depicts a simplified flow diagram of a method for determining characteristics of a feature in accordance with another illustrative embodiment of the present invention. In block 500, a dimensional characteristic of a first grating structure is measured. In block 510, at least a portion of a second feature (e.g., process layer or grating structure) and the first grating structure is illuminated. The second feature is formed over at least a portion of the first grating structure. In block 520, light reflected from the illuminated portion of the second feature and the first grating structure is measured to generate a reflection profile. In block 530, the measured reflection profile is compared to at least one reference reflection profile, the at least one reference reflection profile being selected based on the measured dimensional characteristic of the first grating structure (i.e., generated library or target reflection profile or selected sub-library or target reflection profile). In block 540, a characteristic of the second feature is determined based on the comparison between the measured reflection profile and the selected reference reflection profile.

Returning now to FIG. 1, after receiving the overlay error from the scatterometry tool 130, the controller 140 may take a variety of autonomous actions. The actions may include fault detection and/or process control functions. In one embodiment of the present invention, the controller 140 is adapted to modify the operating recipe of the photolithography tool 120 based on the overlay metric to control operations on subsequently processed wafers. The controller 140 may also use the overlay metric for fault detection. If the amount of overlay error measured is sufficient, the wafer may be reworked (i.e., the photoresist layer is stripped and reformed) prior to performing any additional process steps.

The controller 140 may adjust the recipes for subsequently processed wafers to control the overlay control inputs of the stepper 124. The controller 140 may be configured with a deadband range, in which no corrections are made. The overlay error determined from the overlay metric is compared to a predetermined set of threshold parameters. In one embodiment, the deadband contains a range of error values associated with control input signals centered proximate a set of corresponding predetermined target values. If the overlay error acquired from the scatterometry tool 130 is smaller than its corresponding predetermined threshold value, that particular error is deemed to be in the deadband, and the controller 140 makes no changes to the overlay control inputs. A primary purposes of the deadband is to prevent excessive control actions from causing the semiconductor manufacturing process to be inordinately jittery.

When the controller 140 determines that an error corresponding to an overlay control input signal is not inside the deadband, the overlay error is used to update that overlay control input signal for a photolithography process performed on a subsequent wafer. The controller 140 determines a step size for changing in the value of the overlay control input signal in accordance with a control model. Equation 1 below provides an exemplary control equation for determining a change to an overlay control input signal.

$$\text{New setting} = \text{Old setting} - [(\text{weight}) * (\text{overlay error value})] \quad (1)$$

As illustrated in Equation 1, the controller 140 determines the new setting of the overlay control input signal by subtracting the magnitude of the old setting of the overlay control input signal from the product of the weight and the overlay error value. The weight is a predetermined gain parameter that is assigned to the error value of a particular overlay control input signal. The particular value for the weight may be determined by control simulation or experimentation.

Although the weight value can be used to partially control the step size of the change in the setting of the overlay control input signal, the value of the weight may still be insufficient to prevent an excessively large step size. In other words, even if an optimum weight were to be assigned to a particular error signal, a calculated step size of a change in the setting of a control input signal may be too large, such that it could cause a controller of a semiconductor manufacturing tool to perform in an excessively jittery fashion. Accordingly, the controller 140 may compare the calculated step size to a predetermined maximum step size that is allowable for the change in setting of the overlay control input signal, and thus limit the step size.

One method for using the updated overlay control input signals is implemented using control threads. Control threads can be implemented by the controller 140. Control threads are a significant part of the control scheme of a semiconductor manufacturing tool, such as the stepper 124. Each control thread acts like a separate controller, and is differentiated by various process conditions. For overlay control, the control threads are separated by a combination of different conditions, including the semiconductor manufacturing tool (e.g., stepper 124) currently processing the wafer lot, the semiconductor product, the semiconductor manufacturing operation, and the semiconductor manufacturing tool that processed the semiconductor wafer lot at a previous layer of the wafer.

Control threads account for different semiconductor manufacturing process conditions affect the overlay error in different fashions. By isolating each of the unique semiconductor manufacturing process conditions into its own corresponding control thread, the controller may more accurately evaluate the conditions in which a subsequent semiconductor wafer lot in the control thread will be processed. Since the error measurement is more relevant, changes to the overlay control input signals based upon the error will be more appropriate. The implementation of the control scheme described by the present invention can lead to a reduction in the overlay error.

The effectiveness of the control thread arrangement is illustrated using the following example. Stepper A produces wafers with a translational error of 0.05 microns, Stepper B has an error of –0.05 microns, and Stepper C has 0.1 microns of error. If a semiconductor wafer lot was processed on Stepper A, then it was processed on Stepper B at the next layer, the overlay error between them would be –0.1 microns. If the lot were processed on Stepper B and Stepper C instead, the error would be 0.15 microns. The error is different depending upon which conditions were present when the lot was processed. Below is a table of the possible error outcomes, given the stepper/stepper pair used in processing.

TABLE 1

ERROR AS A FUNCTION OF STEPPER/STEPPER PAIR

|  | Stepper A | Stepper B | Stepper C |
| --- | --- | --- | --- |
| Stepper A | 0 | −0.1 | 0.05 |
| Stepper B | 0.1 | 0 | 0.15 |
| Stepper C | −0.05 | −0.15 | 0 |

One of the advantages of the control thread framework is illustrated in this example. There are three possible overlay error values for each of the steppers, depending upon which stepper processed the wafer lot at the last layer. One problem that arises is the controller cannot predict what the error will be for the next semiconductor wafer lot that is processed on the same semiconductor manufacturing tool. Utilizing the control threads, each of the conditions illustrated in Table 1 would have its own controller. Since only one condition would exist for each controller, that controller would be able to predict the error that the next semiconductor wafer lot could encounter and adjust the control input signals accordingly.

The scatterometry tool 130 provides a measure of the control error. Each of the error measurements corresponds to one of the overlay control input signals. The controller 140 may perform preprocessing or data manipulation activities. One such preprocessing activity is outlier rejection. Outlier rejection is a gross error check that is employed to ensure that the measured overlay error is reasonable in light of the historical performance of the semiconductor manufacturing process. This procedure involves comparing each of the overlay errors to a corresponding predetermined boundary parameter. In one embodiment, even if one of the predetermined boundaries is exceeded, the error data from the entire semiconductor wafer lot may be rejected. To determine the limits of the outlier rejection boundary, thousands of actual semiconductor manufacturing fabrication data points are collected. The standard deviation for each error parameter in this collection of data is then calculated. The boundary threshold is selected as a multiple of the standard deviation (i.e., positive or negative). The selection of the outlier rejection boundary helps ensure that only the points that are significantly outside the normal operating conditions of the process are rejected.

A second preprocessing function the controller 140 may perform is to smooth out or filter the data. Overlay error measurements are subject to a certain amount of randomness. Filtering the overlay error data results in a more accurate assessment of the error in the overlay control input signal settings. In one embodiment, the controller 140 uses an Exponentially-Weighted Moving Average (EWMA) filter to smooth the data, although other filtering procedures may be used. The equation for an EWMA filter is illustrated in Equation 2.

$$\text{New average} = (\text{weight})^*(\text{current measurement}) + (1 - \text{weight})^*(\text{previous EWMA average})] \quad (2)$$

The weight is an adjustable parameter that can be used to control the amount of filtering and generally has a value between zero and one. The weight represents the confidence in the accuracy of the current data point. If the measurement is considered to be accurate, the weight should be close to one. If there were a significant amount of fluctuations in the process for previous processing runs, then a number closer to zero would be appropriate. The new average is calculated from the current measurement, the weight, and the last average calculated. The EWMA filtering process may use the previous average, the weight, and the current measurement as described above, or alternatively, only some of the data (i.e., the most recent) may be used to calculate the average.

The manufacturing environment in the semiconductor manufacturing facility presents some unique challenges. The order that the semiconductor wafer lots are processed through tools, such as the stepper 124, may not correspond to the order in which the scatterometry tool 130 measures the overlay error. Such a situation could lead to data points being added to the EWMA average out of sequence. Also, wafers may be analyzed more than once to verify the error measurements. Without data retention, both readings would contribute to the EWMA average, which may be an undesirable characteristic. Furthermore, some of the control threads may have low volume, which may cause the previous average to be outdated such that it may not be able to accurately represent the error in the overlay control input signal settings. For these reasons, the controller 140 may access stored data to calculate the EWMA filtered error. Semiconductor wafer lot data, including the lot number, the time the lot was processed on the stepper 124, and the multiple error estimates, are stored in a data store under the control thread name. When a new set of overlay error data is collected, the stack of data is retrieved from data store and analyzed. The lot number of the current semiconductor wafer lot being processed is compared to those in the stack. If the lot number matches any of the data present there, the error measurements are replaced. Otherwise, the data point is added to the current stack in chronological order, according to the time periods when the lots were processed through the stepper 124. In some embodiments, data points may expire after a predetermined time period (e.g., 48 hours).

As described above, the controller 140 may be implemented using an APC framework. Deployment of the control strategy taught by the present invention using the APC framework could require a number of software components. In addition to components within the APC framework, a computer script may be written for each of the semiconductor manufacturing tools involved in the control system, such as the stepper 124. When a semiconductor manufacturing tool in the control system is started, it generally initiates control script to complete the actions implemented by the controller 140. The control methods described above are generally defined and performed in these control scripts.

The controller 140 may implement a control technique for a variety of control parameters for the stepper 124, including an x-translation signal, a y-translation signal, an x-expansion wafer scale signal, a y-expansion wafer scale signal, a reticle magnification signal, and a reticle rotation signal. The overlay control model may be developed empirically using commonly known linear or non-linear techniques. The control model may be a relatively simple equation based model, as described above (e.g., linear, exponential, weighted average, etc.), or a more complex model, such as a neural network model, principal component analysis (PCA) model, or a projection to latent structures (PLS) model. The specific implementation of the model may vary depending on the modeling technique selected.

Overlay models may be generated by the controller 140, or alternatively, they may be generated by a different processing resource (not shown) and stored on the controller 140 after being developed. The overlay model may be developed using the stepper 124 or using a different tool (not shown) having similar operating characteristics. For purposes of illustration, it is assumed that the overlay model is generated and updated by the controller 140 or other processing resource based on the actual performance of the stepper 124 as measured by the scatterometry tool 130. The overlay model may be trained based on historical data collected from numerous processing runs of the stepper 124.

The general, two-stage technique is described in reference to FIG. 5, which depicts a simplified flow diagram of a method for determining characteristics of a Mature in accordance with another illustrative embodiment of the present invention. In block 500, a dimensional characteristic of a first grating structure is measured. In block 510, at least a portion of a first feature (e.g., process layer or grating structure) and the first grating structure is illuminated. The first feature is formed over at least a portion of the first grating structure. In block 520, light reflected from the illuminated portion of the first feature and the first grating structure is measured to generate a reflection profile. In block 530, the measured reflection profile is compared to at least one reference reflection profile, the at least one reference reflection profile being selected based on the measured dimensional characteristic of the first grating structure (i.e., generated library or target reflection profile or selected sub-library or target reflection profile). In block 540, a characteristic of the first feature is determined based on the comparison between the measured reflection profile and the selected reference reflection profile.

Monitoring overlay error based on measurements from the scatterometry tool 130, as described above, has numerous advantages. The stepper 124 may be controlled to reduce the amount of variation encountered. Decreased variation reduces the likelihood that a device may be degraded or must be scrapped. Accordingly, the quality of the devices produced on the processing line 100 and the efficiency of the processing line 100 are both increased.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such-variations are considered within the scope and spirit of the invention. Accordingly, the protection sought herein is as set forth in the claims below.

What is claimed:

1. A method for characterizing features, comprising:
    measuring a dimensional characteristic of a first grating structure;
    illuminating at least a portion of a first feature and the first grating structure, the first feature being formed over at least a portion of the first grating structure;
    measuring light reflected from the illuminated portion of the first feature and the first grating structure to generate a reflection profile;
    selecting at least one reference reflection profile based on the measured dimensional characteristic of the first grating structure;
    comparing the generated reflection profile to the selected reference reflection profile; and
    determining a characteristic of the first feature based on the comparison between the measured reflection profile and the selected reference reflection profile.

2. The method of claim 1, wherein forming the first feature further comprises forming a second grating structure over at least a portion of the first grating structure.

3. The method of claim 2, wherein determining the characteristic of the first feature comprises determining an overlay error between the first grating structure and the second grating structure.

4. The method of claim 3, wherein forming the second grating structure further comprises forming a photoresist layer.

5. The method of claim 4, wherein forming the photoresist layer further comprises exposing the photoresist layer to define the second grating structure.

6. The method of claim 4, wherein forming the photoresist layer further comprises developing the photoresist layer to define the second grating structure.

7. The method of claim 1, wherein forming the first feature further comprises forming a process layer over at least a portion of the first grating structure.

8. The method of claim 7, wherein determining the characteristic of the first feature comprises determining a thickness of the process layer.

9. The method of claim 7, wherein determining the characteristic of the first feature comprises determining conformality of the process layer.

10. The method of claim 1, wherein:
    selecting the at least one reference reflection profile further comprises generating a library of reference reflection profiles based on the measured dimension of the first grating structure, each reference reflection profile having an associated characteristic metric;
    comparing the generated reflection profile to the selected reference reflection profile further comprises selecting a reference reflection profile from the library closest to the generated reflection profile; and
    determining the characteristic of the first feature further comprises determining the characteristic of the first feature based on the characteristic metric associated with the selected reference reflection profile from the library.

11. The method of claim 1, wherein:
selecting the at least one reference reflection profile further comprises selecting a set of reference reflection profiles from a library of reference reflection profiles based on the measured dimension of the first grating structure, each reference reflection profile in the selected set having an associated characteristic metric;
comparing the generated reflection profile to the selected reference reflection profile further comprises selecting a reference reflection profile from the set closest to the generated reflection profile; and
determining the characteristic of the first feature further comprises determining the characteristic of the first feature based on the characteristic metric associated with the selected reference reflection profile from the set.

12. The method of claim 1, wherein:
selecting the at least one reference reflection profile further comprises generating a target reflection profile based on the measured dimension of the first grating structure;
comparing the generated reflection profile to the selected reference reflection profile further comprises comparing the generated reflection profile to the target reflection profile; and
determining the characteristic of the first feature further comprises determining the second characteristic of the first feature based on the comparison of the generated reflection profile and the target reflection profile.

13. The method of claim 1, wherein:
selecting the at least one reference reflection profile further comprises selecting a target reflection profile from a library of reference reflection profiles based on the measured dimension of the first grating structure;
comparing the generated reflection profile to the selected reference reflection profile further comprises comparing the generated reflection profile to the target reflection profile; and
determining the characteristic of the first feature further comprising determining the characteristic of the first feature based on the comparison of the generated reflection profile and the target reflection profile.

14. The method of claim 1, wherein generating the reflection profile comprises generating the reflection profile based on at least one of intensity and phase of the reflected light.

15. The method of claim 1, further comprising identifying a fault condition associated with the first feature based on the determined characteristic of the first feature.

16. The method of claim 1, wherein forming the first grating and the first feature further comprises forming the first grating and the first feature in a test structure on a wafer.

17. The method of claim 1, wherein forming the first grating and the first feature further comprises forming the first grating and the first feature in a production device on a wafer.

18. The method of claim 1, wherein measuring the dimension of the first grating structure further comprises measuring the dimension using at least one of a scatterometry tool, a scanning electron microscope, an atomic force microscope, and a thickness measuring tool.

19. A method for characterizing features, comprising:
measuring a dimensional characteristic of a first grating structure;
illuminating at least a portion of a first feature and the first grating structure, the first feature being formed over at least a portion of the first grating structure;
measuring light reflected from the illuminated portion of the first feature and the first grating structure to generate a reflection profile;
generating at least one reference reflection profile based on the measured dimensional characteristic of the first grating structure;
comparing the generated reflection profile to the generated reference reflection profile; and
determining a characteristic of the first feature based on the comparison between the measured reflection profile and the generated reference reflection profile.

20. The method of claim 19, wherein forming the first feature further comprises forming a second grating structure over at least a portion of the first grating structure.

21. The method of claim 20, wherein determining the characteristic of the first feature comprises determining an overlay error between the first grating structure and the second grating structure.

22. The method of claim 21, wherein forming the second grating structure further comprises forming a photoresist layer.

23. The method of claim 22, wherein forming the photoresist layer further comprises exposing the photoresist layer to define the second grating structure.

24. The method of claim 22, wherein forming the photoresist layer further comprises developing the photoresist layer to define the second grating structure.

25. The method of claim 19, wherein forming the first feature further comprises forming a process layer over at least a portion of the first grating structure.

26. The method of claim 25, wherein determining the characteristic of the first feature comprises determining a thickness of the process layer.

27. The method of claim 25, wherein determining the characteristic of the first feature comprises determining conformality of the process layer.

28. The method of claim 19, wherein:
generating the at least one reference reflection profile further comprises generating a library of reference reflection profiles based on the measured dimension of the first grating structure, each reference reflection profile having an associated characteristic metric;
comparing the generated reflection profile to the generated reference reflection profile further comprises selecting a reference reflection profile from the library closest to the generated reflection profile; and
determining the characteristic of the first feature further comprises determining the characteristic of the first feature based on the characteristic metric associated with the selected reference reflection profile from the library.

29. The method of claim 19, wherein:
generating the at least one reference reflection profile further comprises generating a target reflection profile based on the measured dimension of the first grating structure;
comparing the generated reflection profile to the generated reference reflection profile further comprises comparing the generated reflection profile to the target reflection profile; and
determining the characteristic of the first feature further comprises determining the second characteristic of the first feature based on the comparison of the generated reflection profile and the target reflection profile.

30. The method of claim 19, wherein generating the reflection profile comprises generating the reflection profile based on at least one of intensity and phase of the reflected light.

31. The method of claim 19, further comprising identifying a fault condition associated with the first feature based on the determined characteristic of the first feature.

32. The method of claim 19, wherein forming the first grating and the first feature further comprises forming the first grating and the first feature in a test structure on a wafer.

33. The method of claim 19, wherein forming the first grating and the first feature further comprises forming the first grating and the first feature in a production device on a wafer.

34. The method of claim 19, wherein measuring the dimension of the first grating structure further comprises measuring the dimension using at least one of a scatterometry tool, a scanning electron microscope, an atomic force microscope, and a thickness measuring tool.

35. A processing line, comprising:
a first metrology tool adapted to measure a dimensional characteristic of a first grating structure;
a second metrology tool, comprising:
a light source adapted to illuminating at least a portion of a first feature and the first grating structure, the first feature being formed over at least a portion of the first grating structure;
a detector adapted to measure light reflected from the illuminated portion of the first feature and the first grating structure to generate a reflection profile; and
a data processing unit adapted to select at least one reference reflection profile based on the measured dimensional characteristic of the first grating structure, comparing the generated reflection profile to the selected reference reflection profile, and determine a characteristic of the first feature based on the comparison between the measured reflection profile and the selected reference reflection profile.

36. The processing line of claim 35, wherein the first feature further comprises a second grating structure formed over at least a portion of the first grating structure.

37. The processing line of claim 36, wherein the characteristic of the first feature comprises an overlay error between the first grating structure and the second grating structure.

38. The processing line of claim 37, wherein the second grating structure further comprises a photoresist layer.

39. The processing line of claim 38, wherein the photoresist layer further comprises an exposed photoresist layer.

40. The processing line of claim 38, wherein the photoresist layer further comprises a developed photoresist layer.

41. The processing line of claim 35, wherein the first feature further comprises a process layer formed over at least a portion of the first grating structure.

42. The processing line of claim 41, wherein the characteristic of the first feature comprises a thickness of the process layer.

43. The processing line of claim 41, wherein the characteristic of the first feature comprises conformality of the process layer.

44. The processing line of claim 35, wherein the data processing unit is further adapted to generate a library of reference reflection profiles based on the measured dimension of the first grating structure, each reference reflection profile having an associated characteristic metric, select a reference reflection profile from the library closest to the generated reflection profile, and determine the characteristic of the first feature based on the characteristic metric associated with the selected reference reflection profile from the library.

45. The processing line of claim 35, wherein the data processing unit is further adapted to select a set of reference reflection profiles from a library of reference reflection profiles based on the measured dimension of the first grating structure, each reference reflection profile in the selected set having an associated characteristic metric, select a reference reflection profile from the set closest to the generated reflection profile, and determine the characteristic of the first feature based on the characteristic metric associated with the selected reference reflection profile from the set.

46. The processing the of claim 35, wherein the data processing unit is further adapted to generate a target reflection profile based on the measured dimension of the first grating structure, compare the generated reflection profile to the target reflection profile, and determine the second characteristic of the first feature based on the comparison of the generated reflection profile and the target reflection profile.

47. The processing line of claim 35, wherein the data processing unit is further adapted to select a target reflection profile from a library of reference reflection profiles based on the measured dimension of the first grating structure, compare the generated reflection profile to the target reflection profile, and determine the characteristic of the first feature based on the comparison of the generated reflection profile and the target reflection profile.

48. The processing line of claim 35, wherein the detector is further adapted to generate the reflection profile based on at least one of intensity and phase of the reflected light.

49. The processing line of claim 35, further comprising a controller adapted to identify a fault condition associated with the first feature based on the determined characteristic of the first feature.

50. The processing line of claim 35, wherein the first grating structure and the first feature are formed in a test structure on a wafer.

51. The processing line of claim 35, wherein the first grating structure and the first feature are formed in a production device on a wafer.

52. The processing line of claim 35, wherein the first metrology tool comprises at least one of a scatterometry tool, a scanning electron microscope, an atomic force microscope, and a thickness measuring tool.

53. A processing line, comprising:
a first metrology tool adapted to measure a dimensional characteristic of a first grating structure;
a second metrology tool, comprising:
a light source adapted to illuminating at least a portion of a first feature and the first grating structure, the first feature being formed over at least a portion of the first grating structure;
a detector adapted to measure light reflected from the illuminated portion of the first feature and the first grating structure to generate a reflection profile; and;
a data processing unit adapted to generate at least one reference reflection profile based on the measured dimensional characteristic of the first grating structure, compare the generated reflection profile to the generated reference reflection profile, and determine a characteristic of the first feature based on the comparison between the measured reflection profile and the generated reference reflection profile.

54. The processing line of claim 53, wherein the first feature further comprises a second grating structure formed over at least a portion of the first grating structure.

55. The processing line of claim 54, wherein the characteristic of the first feature comprises an overlay error between the first grating structure and the second grating structure.

56. The processing line of claim 55, wherein the second grating structure further comprises a photoresist layer.

57. The processing line of claim 56, wherein the photoresist layer further comprises an exposed photoresist layer.

58. The processing line of claim 56, wherein the photoresist layer further comprises a developed photoresist layer.

59. The processing line of claim 53, wherein the first feature further comprises a process layer formed over at least a portion of the first grating structure.

60. The processing line of claim 59, wherein die characteristic of the first as feature comprises a thickness of the process layer.

61. The processing line of claim 59, wherein the characteristic of the first feature comprises conformality of the process layer.

62. The processing line of claim 53, wherein the data processing unit is further adapted to generate a library of reference reflection profiles based on the measured dimension of the first grating structure, each reference reflection profile having an associated characteristic metric, select a reference reflection profile from the library closest to the generated reflection profile, and determine the characteristic of the first feature based on the characteristic metric associated with the selected reference reflection profile from the library.

63. The processing line of claim 53, wherein the data processing unit is further adapted to generate a target reflection profile based on the measured dimension of the first grating structure, compare the generated reflection profile to the target reflection profile, and determine the second characteristic of the first feature based on the comparison of the generated reflection profile and the target reflection profile.

64. The processing line of claim 53, wherein the detector is further adapted to generate the reflection profile based on at least one of intensity and phase of the reflected light.

65. The processing line of claim 5, further comprising a controller adapted to identify a fault condition associated with the first feature based on the determined characteristic of the first feature.

66. The processing line of claim 53, wherein the first grating structure and the first feature are formed in a test structure on a wafer.

67. The processing line of claim 53, wherein the first grating structure and the first feature are formed in a production device on a wafer.

68. The processing line of claim 53, wherein the first metrology tool comprises at least one of a scatterometry tool, a scanning electron microscope, an atomic force microscope, and a thickness measuring tool.

69. A processing line, comprising:

means for measuring a dimensional characteristic of a first grating structure;

means for illuminating at least a portion of a first feature and the first grating structure, the first feature being formed over at least a portion of the first grating structure;

means for measuring light reflected from the illuminated portion of the first feature and the first grating structure to generate a reflection profile;

means for selecting at least one reference reflection profile based on the measured dimensional characteristic of the first grating structure;

means for comparing the generated reflection profile to the selected reference reflection profile; and means for determining a characteristic of the first feature based on the comparison between the measured reflection profile and the selected reference reflection profile.

70. A processing line, comprising:

means for measuring a dimensional characteristic of a first grating structure;

means for illuminating at least a position of a first feature and the first grating structure, the first feature being formed over at least a portion of the first grating structure;

means for measuring light reflected from the illuminated portion of the first feature and the first grating structure to generate a reflection profile;

means for generating at least one reference reflection profile based on the measured dimensional characteristic of the first grating structure;

means for comparing the generated reflection profile to the generated reference reflection profile; and means for determining a characteristic of the first feature based on the comparison between the measured reflection profile and the generated reference reflection profile.

* * * * *

UNITED STATES PATENT AND TRADEMARK OFFICE
CERTIFICATE OF CORRECTION

PATENT NO.    : 6,614,540 B1                                                  Page 1 of 1
DATED         : September 2, 2003
INVENTOR(S)   : James B. Stirton It is certified that error appears in the above-identified patent and that said Letters Patent is hereby corrected as shown below:

Column 15,
Line 40, replace "comprising" with -- comprises --.

Column 18,
Line 9, replace "the of" with -- line of --.

Column 19,
Line 8, replace "die" with -- the --.
Line 34, replace "5" with -- 53 --.

Column 20,
Line 27, replace "position" with -- portion --.

Signed and Sealed this

Twenty-third Day of December, 2003

JAMES E. ROGAN
*Director of the United States Patent and Trademark Office*